(12) United States Patent
Rourke

(10) Patent No.: US 7,819,882 B2
(45) Date of Patent: *Oct. 26, 2010

(54) STENT DELIVERY DEVICE

(75) Inventor: Jonathan M Rourke, Belmont, MA (US)

(73) Assignee: Boston Scientific Cupertino Corporation, Cupertino, CA (US)

( * ) Notice: Subject to any disclaimer, the term of this patent is extended or adjusted under 35 U.S.C. 154(b) by 926 days.

This patent is subject to a terminal disclaimer.

(21) Appl. No.: 11/355,284

(22) Filed: Feb. 14, 2006

(65) Prior Publication Data

US 2006/0167467 A1    Jul. 27, 2006

Related U.S. Application Data

(63) Continuation of application No. 10/373,500, filed on Feb. 24, 2003, now Pat. No. 7,033,368, which is a continuation of application No. 09/613,872, filed on Jul. 10, 2000, now Pat. No. 6,527,779.

(51) Int. Cl.
*A61F 11/00* (2006.01)
(52) U.S. Cl. ..................................... 606/108; 623/1.11
(58) Field of Classification Search ................. 606/108; 604/93.01; 623/1.11; 222/236, 325–327, 222/153.01–153.14; 600/7
See application file for complete search history.

(56) References Cited

U.S. PATENT DOCUMENTS

| 4,473,076 | A | * | 9/1984 | Williams et al. ............. 606/172 |
| 4,615,469 | A | * | 10/1986 | Kishi et al. ................. 222/327 |
| 4,669,636 | A | * | 6/1987 | Miyata ................... 222/153.01 |
| 4,986,454 | A | * | 1/1991 | Riley ........................... 222/327 |
| 5,290,310 | A |   | 3/1994 | Makover et al. |
| 5,306,284 | A | * | 4/1994 | Agee et al. ................... 606/170 |
| 5,322,240 | A | * | 6/1994 | Sato ........................... 242/302 |
| 5,372,323 | A | * | 12/1994 | Hirano et al. ................ 242/299 |
| 5,381,931 | A | * | 1/1995 | Chang ........................ 222/309 |

(Continued)

FOREIGN PATENT DOCUMENTS

EP          0 873 733 A1    10/1998

(Continued)

OTHER PUBLICATIONS

EPO Publication No. EP 0 990 426 A1, entitled "Disposable Delivery Device for Endoluminal Prosthesis," Apr. 5, 2000.

*Primary Examiner*—Darwin P Erezo
(74) *Attorney, Agent, or Firm*—Vidas, Arrett & Steinkraus P.A.

(57) ABSTRACT

A unidirectional handle device for an endoluminal device includes an outer tubular member and an elongate inner member slidably received in the outer tubular member. The unidirectional handle includes a handle member, a needle bearing clutch disposed in the handle member, a control member guide, and shaft rotatable in a single direction disposed within the handle member. The shaft is rotatable in a single direction by its engagement with the needle bearing clutch. The shaft is in rotational engagement with the outer tubular member of the endoluminal device. The outer tubular member is slidable from a distal position to a proximal position when the shaft is rotated in the single direction. The unidirectional handle device provides substantially no backlash of the outer tubular member. In addition, the unidirectional handle device advantageously produces a tension-retaining effect during use.

8 Claims, 3 Drawing Sheets

U.S. PATENT DOCUMENTS

| | | | |
|---|---|---|---|
| 5,391,172 A | 2/1995 | Williams et al. | |
| 5,409,478 A | 4/1995 | Gerry et al. | |
| 5,433,723 A | 7/1995 | Lindenberg et al. | |
| 5,601,568 A | 2/1997 | Chevillon et al. | |
| 5,697,948 A | 12/1997 | Marin et al. | |
| 5,707,376 A | 1/1998 | Kavteladze et al. | |
| 5,759,186 A | 6/1998 | Bachmann et al. | |
| 5,762,239 A * | 6/1998 | Cossette | 222/326 |
| 5,775,539 A * | 7/1998 | Bates et al. | 222/1 |
| 5,833,694 A | 11/1998 | Poncet | |
| 5,868,755 A | 2/1999 | Kanner et al. | |
| 5,906,619 A | 5/1999 | Olson et al. | |
| 5,968,052 A * | 10/1999 | Sullivan et al. | 623/1.11 |
| 5,993,188 A * | 11/1999 | Mak | 425/376.1 |
| 6,036,130 A * | 3/2000 | Tietjen | 242/256 |
| 6,053,934 A | 4/2000 | Andrews et al. | |
| 6,123,235 A * | 9/2000 | Hsu | 222/327 |
| 6,143,021 A | 11/2000 | Staehle | |
| 6,383,211 B1 | 5/2002 | Staehle | |
| 6,527,779 B1 * | 3/2003 | Rourke | 606/108 |
| 7,033,368 B2 * | 4/2006 | Rourke | 606/108 |
| 2005/0029292 A1 * | 2/2005 | Ophardt | 222/94 |

FOREIGN PATENT DOCUMENTS

| | | |
|---|---|---|
| EP | 0 876 804 A1 | 11/1998 |
| WO | 96/18361 A1 | 6/1996 |
| WO | WO99/49808 | 10/1999 |

* cited by examiner

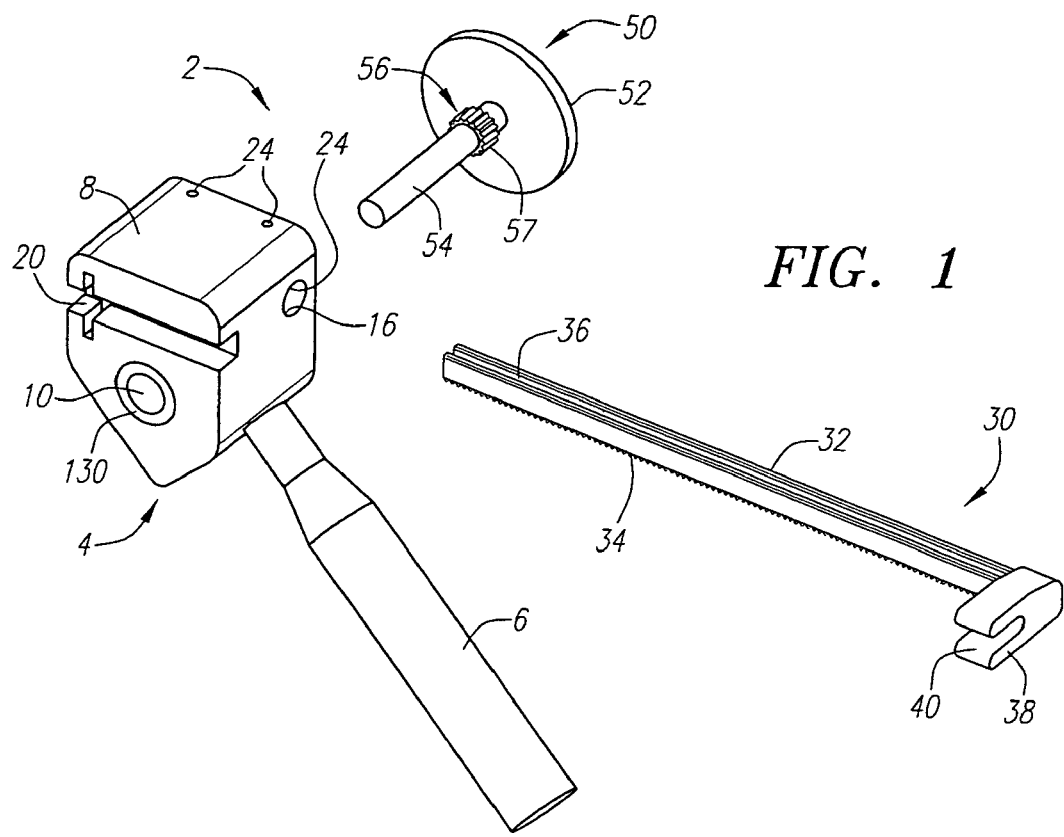
FIG. 1
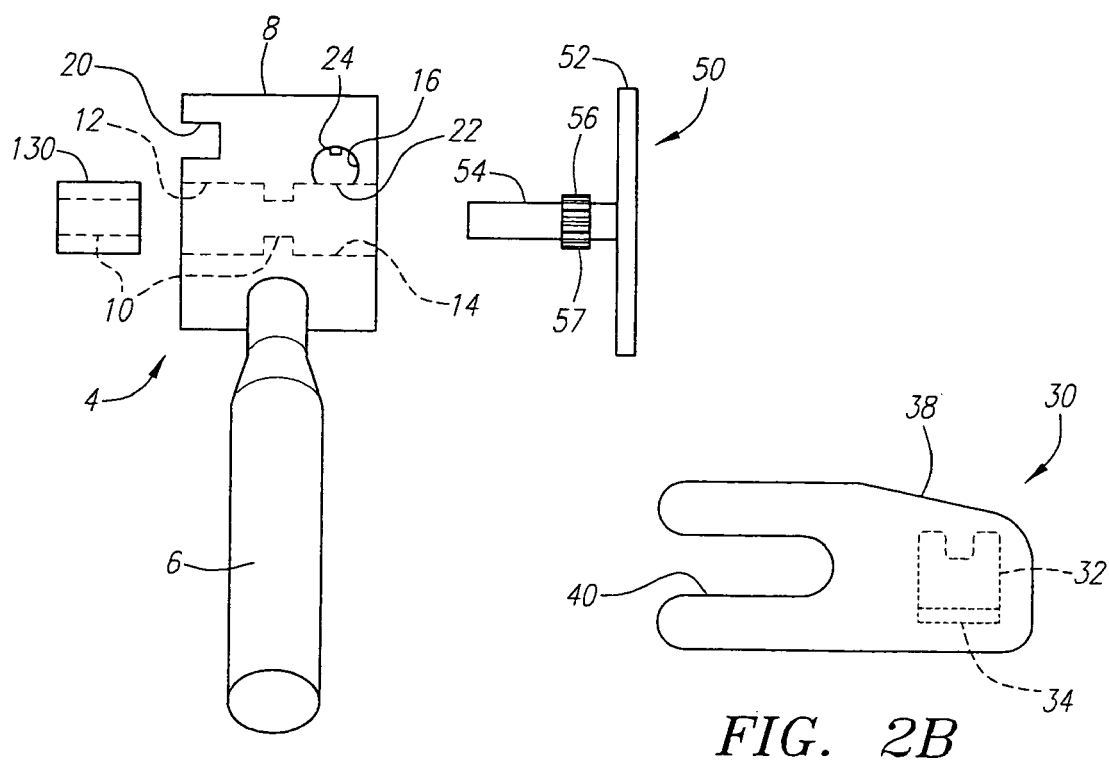
FIG. 2A
FIG. 2B

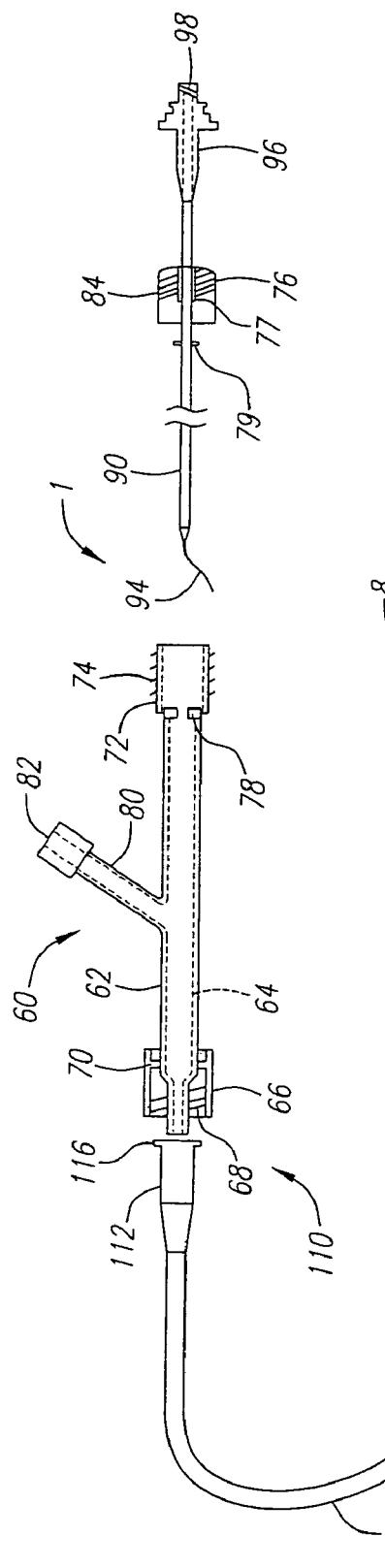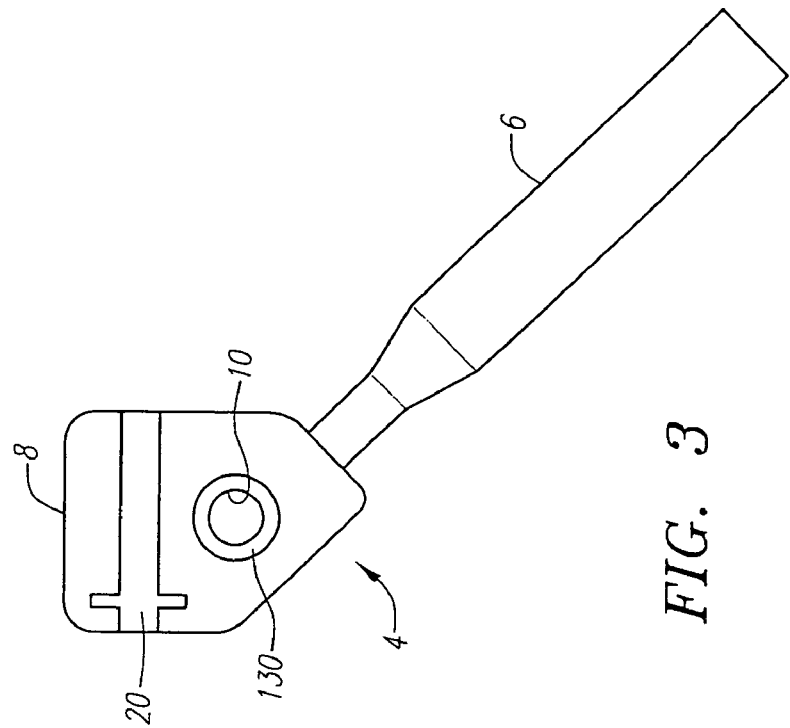
FIG. 3
FIG. 4

STENT DELIVERY DEVICE

RELATED APPLICATION DATA

This application is a continuation of U.S. patent application Ser. No. 10/373,500, filed Feb. 24, 2003, now U.S. Pat. No. 7,033,368, which is a continuation of application Ser. No. 09/613,872, filed Jul. 10, 2000, now U.S. Pat. No. 6,527,779, the disclosures of which is expressly incorporated herein by reference.

FIELD OF THE INVENTION

The present invention relates generally to catheter-based systems for treating a remote location within a patient, and more particularly to handles for stent delivery systems, electrophysiology devices and the like, which include a catheter and a retractable sheath thereon.

BACKGROUND OF THE INVENTION

Devices having a retractable sheath associated with a catheter are used to treat a variety of conditions using endoluminal methods instead of open surgical procedures. For example, angioplasty and stent implantation procedures are often used to treat atherosclerotic disease or other occlusive conditions in blood vessels, such as the coronary and carotid arteries. During angioplasty, for example, a catheter having an uninflated balloon on its distal end is percutaneously introduced into a patient's vasculature and advanced to a target treatment location, such as a stenosis within a blood vessel. Once the balloon is properly placed across the stenosis, the balloon is inflated to enlarge the lumen at the location. The balloon is then deflated, the inflation/deflation procedure may be repeated, and then the catheter is then withdrawn from the patient's body.

Often in conjunction with angioplasty, a stent or other tubular prosthesis may be implanted within a stenosis to scaffold the location and prevent it from contracting or otherwise becoming obstructed again. The stent, in a contracted condition, is generally placed upon a catheter, possibly over a balloon. The catheter is advanced to the target stenosis until the stent is adjacent to the location, and then the stent is deployed and substantially anchored at the location. The stent may be biased to expand to an enlarged condition and/or may be expanded with the aid of a balloon, as with plastically deformable stents, until the stent substantially engages the wall of the vessel. Once the stent is implanted, the delivery catheter is withdrawn from the patient.

Similarly for ablation procedures and the like, a catheter including an array of electrodes, for example, on an expandable basket assembly, may be provided. The device may be introduced into a body lumen, for example through the patient's vasculature into the heart, to treat conditions, such as heart arrhythmia.

With any of these systems, a sheath may be provided over the distal end of the catheter to protect the components on the distal end, such as a balloon, a stent, an array of electrodes, and the like. The sheath may be advanced distally over the proximal end of the catheter until it covers the distal end and its components, or, alternatively, the distal end of the catheter may be introduced into the sheath, and advanced until it is proximate the distal end of the sheath. Once the distal end of the catheter is properly positioned at a desired location within a body lumen, the sheath may be retracted to expose the distal end of the catheter. After treatment, the sheath may be advanced back over the distal end of the catheter, and the entire device withdrawn from the patient.

To cause the sheath to retract, the proximal end of the sheath outside the patient may simply be pulled while holding the catheter in a fixed position. This, however, may not provide very precise control of the retraction of the sheath. To provide improved control, handle devices have been proposed that include a wheel and screw mechanism. A wheel extending around the circumference of the handle is coupled to a screw mechanism engaging the sheath and the catheter. As the wheel is rotated about the longitudinal axis of the handle, the screw mechanism directs the sheath axially with respect to the catheter.

With such devices, however, it may be difficult to remember which direction, i.e., clockwise or counterclockwise, is appropriate either to retract or advance the sheath with respect to the catheter. This may be particularly important when immediate action is necessary because of a complication during a procedure. Moreover, in such devices, it is possible to advance the sheath in the distal direction during and after deployment of the device, such as a stent, on the distal end of the catheter. This distal movement may result in the improper placement and unwanted movement of the deployed device. This distal movement of the sheath is particularly problematic in the deployment of stents or other tubular prostheses. It is preferred that a catheter-sheath system have only unidirectional motion, i.e., only permit retraction of the sheath in the proximal direction.

Another disadvantage in current screw-type devices is that the devices are often complicated, including many parts which may be difficult to assemble and/or expensive to make.

Accordingly, there is a need for more intuitive, more simple, and/or less expensive devices for controlling catheter-sheath systems.

SUMMARY OF THE INVENTION

In a first aspect of the invention, a unidirectional handle device for an endoluminal device includes an outer tubular member and an elongate inner member slidably received in the outer tubular member. The elongate inner member is detachably mounted to the unidirectional handle device. The unidirectional handle device includes a handle member, a needle bearing clutch disposed in the handle member, a control member guide in the handle member, and a shaft. The shaft is disposed in the handle member and rotatable in a single direction. The shaft engages with the needle bearing clutch and is in rotational engagement with the outer tubular member. The outer tubular member is slidable from a distal position to a proximal position when the shaft is rotated in the single direction.

In another aspect of the invention, the unidirectional handle includes a handle member, a needle bearing clutch disposed in the handle member, a control member slidably disposed in the handle member, and a shaft. The control member is mounted at one end thereof to the outer tubular member. The shaft is mounted to the handle member and rotatable in a single direction by engaging with the needle bearing clutch. The shaft further includes a gear mounted thereon, wherein the gear is engaged with the control member. The control member is slidable from a distal position to a proximal position and not slidable from a proximal position to a distal position.

In still another aspect of the invention, the unidirectional handle device includes a handle member including a grip portion and a body portion. The body portion includes a transverse bore and a control member guide therein. A needle bearing clutch is disposed in a clutch recess located in the body portion, the needle bearing clutch and the clutch recess are coaxial with the transverse bore. A control member is slidably moveable within the control member guide of the body portion with the control member engaged at one end with the outer tubular member. The handle device includes a control knob including a shaft and gear thereon. The shaft engages with the needle bearing clutch while the gear engages with the control member. The control member is slidable from a distal position to a proximal position.

In still another aspect of the invention, the handle device includes a handle member, a needle bearing clutch disposed in the handle member, and a control member slidably disposed in the handle member. The control member is mounted at one end thereof to a hydrostatic valve assembly. A control knob is mounted to the handle member and rotatable in a single direction, the control knob including a shaft engaging with the needle bearing clutch. The shaft further includes a gear engaged with the control member, the control member being slidable from a distal position to a proximal position and not slidable from a proximal position to a distal position.

In yet another aspect of the invention, a unidirectional handle device for an endoluminal device includes an outer tubular member and an elongate inner member slidably received in the outer tubular member. The unidirectional handle includes a handle member including a grip portion and a body portion, the body portion including a transverse bore and a control member guide therein. The body portion further includes an inner member recess for detachably mounting the elongate inner member. A needle bearing clutch is disposed in a clutch recess located in the body portion, wherein the needle bearing clutch and the clutch recess are coaxial with the transverse bore. A control member is slidably moveable within the control member guide of the body portion, the control member further includes a rail portion including a plurality of teeth thereon. The control member is releasably engaged at one end thereof with the outer tubular member. A control knob is provided and includes a shaft and gear thereon. The shaft engages with the needle bearing clutch and the gear engages with the teeth of the rail portion. The control member is slidable from a distal position to a proximal position and not slidable from a proximal position to a distal position.

In another separate aspect of the invention, a catheter-sheath system for delivering a stent to a patient includes an outer tubular member, an elongate inner member slidably received in the outer tubular member, and a handle device for imparting unidirectional movement of the outer tubular member relative the elongate inner member. The handle includes a handle member, a needle bearing clutch disposed in the handle member, a control member slidably disposed in a control member guide in the handle member. The control member is engaged at one end thereof to the outer tubular member. A control knob is mounted to the handle member and rotatable in a single direction. The control knob includes a shaft engaging with the needle bearing clutch. The shaft further includes a gear engaged with the control member, the control member being slidable from a distal position to a proximal position and not slidable from a proximal position to a distal position.

BRIEF DESCRIPTION OF THE DRAWINGS

FIG. 1 is an exploded view of the handle device showing the handle member, one aspect of the control member, and the control knob.

FIG. 2(a) is an end view of the handle device showing the handle member, the roller bearing clutch, and the control knob.

FIG. 2(b) is an end view of one aspect of the control member.

FIG. 3 is a side view of the handle member.

FIG. 4 is a side view of an endoluminal device showing the outer tubular member, the hemostatic valve assembly, and the elongate inner member.

DETAILED DESCRIPTION OF THE PREFERRED EMBODIMENTS

Figure 5A:
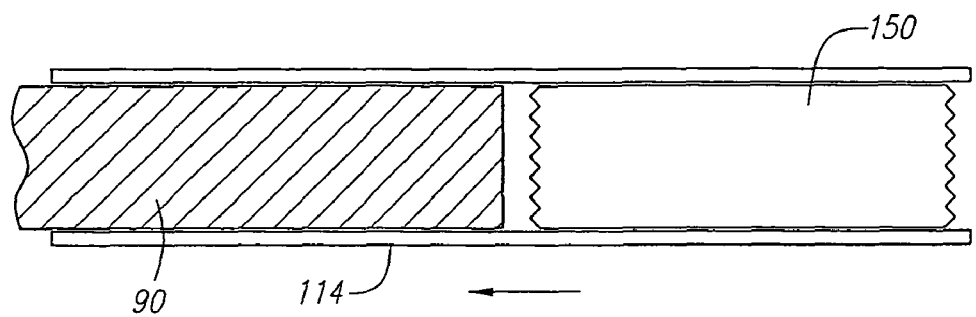
FIG. 5(a) is an enlarged side view of a stent contained within the outer tubular member and the elongate inner member disposed adjacent to the stent.

Turning now in detail to the drawings, FIGS. 1, 3, and 4 show a handle device 2 in accordance with the invention that may include as few as three parts, namely, a handle member 4, a shaft 54, and needle bearing clutch 130.

In one preferred embodiment of the invention, the handle device 2 includes a handle member 4, a control knob 50, and a control member 30. The handle member 4, control knob 50, and control member 30 can be made of materials such as molded or machined plastic, or stainless steel. Any material commonly used within the medical device field can be used in the handle device 2.

Turning in more detail to the handle member 4, the handle member 4 preferably comprises a grip portion 6 and a body portion 8. The grip portion 6 is generally tubular in shape and projects from the body portion 8 at an oblique angle. In use, the grip portion 6 preferably extends in a forward or distal direction away from the user.

Referring to FIGS. 1, 2, and 3, the body portion 8 includes a transverse bore 10 passing through the entire body portion 8, As best seen in FIG. 2, a needle bearing clutch recess 12 and a gear recess 14 are located on opposing sides of the body portion 8. Both the needle bearing clutch recess 12 and the gear recess 14 are coaxial with the transverse bore 10.

Also located within the body portion 8 is a control member guide 16. The control member guide 16 preferably passes entirely through the body portion 8. In this manner, the control member guide 16 is preferably a bore through the body portion 8. It should be understood, however, that the control member guide 16 can be located on a side of the body portion 8 (having one side exposed to the outside environment) or the control member guide 16 can be a separate component external to the body portion 8. In addition, the control member guide 16 is preferably substantially perpendicular to the transverse bore 10. Of course, other orientations of the transverse bore 10 and control member guide 16 are possible, i.e., parallel, angular, and the like, and are intended to fall within the scope of the invention.

Referring now to FIGS. 1 and 2, the control member guide 16 preferably has one or more guide pins 24 projecting therein. The guide pins 24 preferably are affixed to the body portion 8. The guide pins 24 slidably engage with a groove 36 located in the control member 30 when the control member 30 is positioned inside the control member guide 16. The control member guide 16 also includes an opening 22 therein, as shown in FIG. 2, in communication with the gear recess 14. The opening 22 allows the gear 56 of the control knob 50 to engage with teeth 34 of the control member 30. In this way, movement of the control knob 50 controls movement of the control member 30.

Referring to FIGS. 1, 2, and 3, the body portion 8 of the handle member 4 includes an inner member recess 20 along one side of the body portion 8. The inner member recess 20 is used to detachably mount an elongate inner member 90. The elongate inner member 90 is preferably press-fit into the inner member recess 20 by the user. In this manner, the elongate inner member 90 is fixed relative to the handle device 2. The elongate inner member 90 can comprise any number of structures such as, by way of illustration and not limitation, catheters, guidewires, bumpers, and the like. With reference to FIG. 4, the elongate inner member 90 includes at a proximal end thereof a proximal attachment member 96. The proximal attachment member 96 is press-fit or the like into the inner member recess 20. The proximal attachment member 96 advantageously has a corresponding profile and geometry as the inner member recess 20. In this regard, the elongate inner member 90 is properly secured to the handle device 2. Threads 98 or other connectors may be located on a proximal end of the proximal attachment member 96 so the elongate inner member 90 may attach to additional devices (not shown).

With reference to FIG. 4, a description of the components of one example of an endoluminal device 1 will now be described. The endoluminal device 1, in its most general format, can comprise an elongate inner member 90 and an outer tubular member 110. In FIG. 4, the outer tubular member 110 includes a flexible sheath 114 and a separate hemostatic valve assembly 60. It should be understood, however, that the outer tubular member 110 can comprise only one component such as flexible sheath 114 or the like.

Flexible sheath 114 includes a lumen therein (not shown) for the passage of the elongate inner member 90. The flexible sheath may include a generally cone-shaped proximal transition member 112 to aid in fastening the flexible sheath 114 to the hemostatic valve assembly 60.

The hemostatic valve assembly 60 has a generally tubular body 62 having a central lumen 64 therein. The central lumen 64 is in fluid communication with the lumen of the proximal transition member 112 (not shown) and flexible sheath 114 lumen (not shown) when attached to the hemostatic valve assembly 60. The hemostatic valve assembly 60 preferably includes an optional flush port 80 having a flush lumen 82 therein that is in fluid communication with the central lumen 64 of the hemostatic valve assembly 60. The flush port 80 may be used to introduce fluid into the flush lumen 82 and central lumen 64 as will be appreciated by those skilled in the art. A distal engagement member 66 is located at the distal end of the hemostatic valve assembly 60. The distal engagement member 66 is preferably rotational about its axis. The distal engagement member 66 is sealed with respect to the hemostatic engagement member 60 via seal 70. The distal engagement member 66 includes threads 68 that engage in a sealed fashion with corresponding threads 116 on the proximal transition member 112 of the flexible sheath 114.

The proximal end of the hemostatic valve assembly 60 includes a proximal engagement member 72 that has a generally tubular construction. On the exterior of the proximal engagement member 72 are located a plurality of threads 74. A seal 78 is affixed inside the hemostatic valve assembly 60 adjacent to the proximal engagement member 72.

Still referring to FIG. 4, the endoluminal device 1 comprises an elongate inner member 90. A catheter is shown in FIG. 4 as the elongate inner member 90. Preferably, the elongate inner member 90 includes a lumen therein (not shown) such that a guidewire or the like can be used to feed and position the elongate inner member 90 into the vasculature of a patient. An end cup 76 surrounds the elongate inner member 90 when positioned inside the hemostatic valve assembly 60. The end cup 76 includes an internal tubular projection 77 therein having a lumen for the passage of the elongate inner member 90. A seal 79 is advantageously located distal to the end cup 76. Threads 84 are located inside the end cup 76. During operation, the elongate inner member 90 is fed through the internal tubular projection 77 of the end cup 76, through the seals 78, 79, and into the central lumen 64 of the hemostatic valve assembly 60. When the end cup 76 is screwed onto the proximal engagement member 72, a seal is formed at the proximal end of the hemostatic assembly 60. A sealing engagement is made by compressing the seal 79 between the seal 78 and the tubular projection 77.

An optional flexible tip 94 can be affixed to the end of the elongate inner member 90 when the elongate member is not used as a bumper, i.e., when a stent 150 is placed distal to the elongate inner member 90 inside the flexible sheath 114. The flexible tip 94, when used, includes a lumen therein (not shown) so a guidewire or the like can pass through.

The proximal end of the elongate inner member 90 is attached to the proximal attachment member 96. The proximal attachment member also includes a lumen therein (not shown) in communication with the lumen of the elongate inner member 90. When a guidewire or the like is used, it is fed into the elongate inner member 90 through the proximal attachment member 96.

Referring now to FIGS. 1 and 2, the control knob 50 and control member 30 will now be described. The control knob 50 preferably includes a general circular wheel portion 52. While a circular-shaped wheel 52 is preferred, other shapes and geometries are possible and within the scope of the invention. A shaft 54 projects in one direction from the wheel 52 and is fixedly secured thereto. The shaft 54 projects generally perpendicular to the plane of the wheel 52. The diameter of the shaft 54 is approximately equal to the inner diameter of the transverse bore 10. A gear 56 is fixedly secured onto the shaft 54 and includes a plurality of teeth 57. During operation, the control knob 50 is inserted into the handle device 2. The shaft 54 passes through the transverse bore 10 and into a needle-bearing clutch 130 located therein. While the control knob 50 is preferred due to the incorporation of the wheel portion 52, it should be appreciated that the handle device 2 may operate within the scope of the invention using only a shaft 54.

The control member 30 preferably includes a rail 32 and an engagement member 38. The rail 32 includes a groove 36 on the upper side thereof. The groove 36 engages with guide pins 24 in the handle member 4 when the control member 30 is inserted into the handle device 2. Teeth 34 are located along the underside of the rail 32. The teeth 34 engage with corresponding teeth 57 of the gear 56 of the control knob 50 when the control member 30 is positioned inside the handle device 2 with the control knob 50 in place. At one end of the rail 32 is located an engagement member 38. The engagement member 38 includes a recess 40 therein for engaging with the outer tubular member 110 or hemostatic valve assembly 60. As shown in FIGS. 1 and 2, the recess 40 engages with the tubular body 62 of the hemostatic valve assembly 60. In this embodiment, the engagement member 38 snaps-on and/or is press-fit onto the hemostatic valve assembly 60. It should be understood, however, that the engagement member 38 can directly affix to the outer tubular member 110 on any component or structure secured to the outer tubular member 110. The engagement member 38 and in a more general sense the control member 30 serve to forcibly move the outer tubular member 110 relative to the fixed elongate inner member 90.

FIGS. 1, 2, and 3 show the needle bearing clutch 130. The needle bearing clutch 130 has an outer chamber diameter substantially equal to the needle bearing clutch recess 12. The needle bearing clutch 130 is secured to the body portion 8 of the handle device 2 by press-fitting or through use of an adhesive or the like. The needle bearing clutch 130 generally includes a plurality of needle rollers held within a cage inside an outer cup. Springs are associated with each of the needle rollers. The needle bearing clutch 130 is designed to transmit torque between the shaft 54 and the needle bearing clutch 130 in one direction and allow free overrun in the opposite direction. Generally, precisely formed interior ramps provide surfaces against which the needle rollers wedge to positively transmit a locking torque when the shaft 54 is turned in one direction. The needle bearing clutch 130 is preferably obtained from the Torrington Company, 59 Field Street, P.O. BOX 1008, Torrington, Conn. 06790-1008. The needle bearing clutch 130 advantageously permits the transition from overrun (rotation) to lock with minimal lost motion or backlash. In this regard, the handle device 2 has substantially no backlash motion of the outer tubular member 110. Substantially no backlash is meant to indicate that there is no appreciable movement of the outer tubular member 110 in the distal direction that would destroy the tension-retaining effect of the handle device 2. This anti-backlash feature is particularly advantageous for the clinical deployment of self-expanding stents 150. Specifically, the anti-backlash feature prevents the flexible sheath 114 or outer tubular member 110 from "springing back" if the clinician stops the motion or releases the input torque on the control knob 50. In this fashion, the needle bearing clutch 130 provides for slow, controlled retraction of the outer tubular member 110 or flexible sheath 114.

Figure 5B:
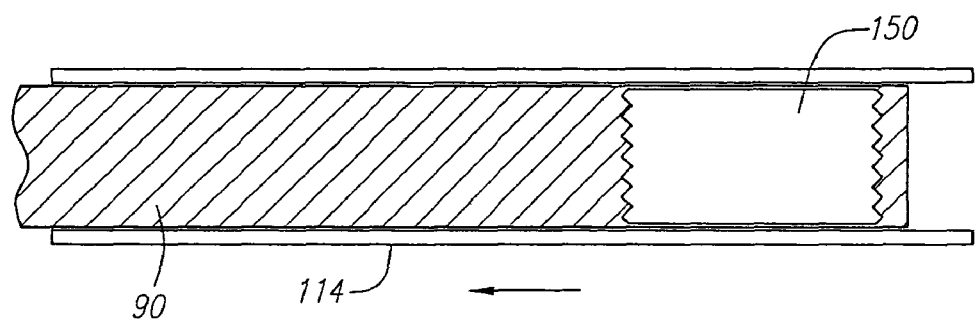
FIG. 5(b) is an enlarged side view of a stent contained within the outer tubular member, wherein the stent is located on the elongate inner member.

FIGS. 5(a) and 5(b) show a close-up view of the distal end of the flexible sheath 114 containing a loaded stent 150 and elongate inner member 90. In FIG. 5(a), the stent 150 is loaded adjacent to the elongate inner member 90. In this manner, the elongate inner member 90 acts as a bumper, wherein the distal end abuts the end of the stent 150 during stent 150 deployment.

In FIG. 5(b), the stent 150 is loaded on the elongate inner member 90. The stent 150 thus surrounds the elongate inner member 90. The configurations shown in FIGS. 5(a) and 5(b) are within the scope of the invention.

A description will now be given of the operation of the handle device 2. For ease of description, it is assumed that the stent 150 or other device is loaded and the elongate inner member 90 is within the outer tubular member 110 or flexible sheath 114. Initially, the elongate inner member 90 is secured to the body portion of the handle member 4 by pressing the proximal attachment member 96 into the inner member recess 20. The elongate inner member 90 is thus fixed (in the axial direction) with respect to the handle device 2. In one aspect of the invention, the control member 30, which is located within the control member guide 16, is then affixed to the outer tubular member 110. If a hemostatic valve assembly 60 is used, the control member 30 is attached to the hemostatic valve assembly 60. At this point, the control knob 50 is in position within the handle device 2 with the shaft 54 engaging with the needle bearing clutch 130. The teeth 57 of the gear 56 are engaged with the corresponding teeth 34 of the rail 32. During deployment of the stent 150, the outer tubular member 110 is retracted in the proximal direction, while the elongate inner member 90 remains fixed in the axial direction. The control knob 50, which is rotatable in only one direction due to the needle bearing clutch 130, retracts the control member 30 within the handle device 2. The outer tubular member 110, which is engaged with the control member 30, is retracted as well. The outer tubular member 110 is retracted until the stent 150 or other device is deployed. Since the shaft 54 of the control knob 50 engages with the needle bearing clutch 130, the control knob 50 turns in only one direction to retract the outer tubular member 110 in the proximal direction. It should be appreciated that the handle device 2 is unidirectional in that the outer tubular member 110 is only moveable in one direction, the proximal direction, relative to the elongate inner member 90.

The unidirectional aspect of the handle device 2 provides several benefits. Initially, the handle device 2 prevents a user from accidentally moving the outer tubular member 110 in the distal direction. In this manner, the outer tubular member 110 cannot collide or push a stent 150 that has already deployed. In addition, the outer tubular member 110 is in constant tension during retraction when the handle device 2 is used. This tension-retaining feature is particularly important because the outer tubular member 110, and in particular the flexible sheath 114, have a tendency to stretch to some extent. With the handle device 2 described herein, when the outer tubular member 110 or flexible sheath 114 is retracted a certain distance by rotation of the control knob 50 and let go, the tension or stretch in the outer tubular member 110 or flexible sheath 114 remains. It is generally preferable to retain this tension in the outer tubular member 110. Existing devices may not have this tension-retaining effect and recoil to a certain extent, once movement of the sheath stops. In prior devices, the sheath has a tendency to deform or change the shape once retraction has stopped.

Figure 6:
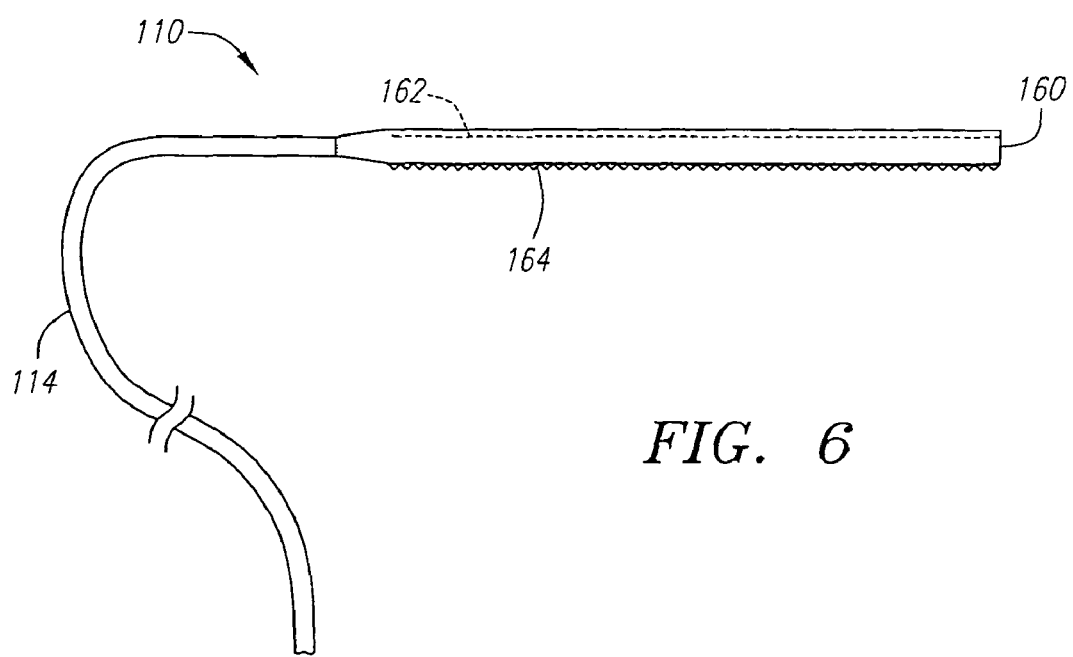
FIG. 6 is a side view of one embodiment of the control member and outer tubular member.

FIG. 6 illustrates another aspect of the invention. In this aspect, the outer tubular member 110 includes at a proximal end thereof, a control member 160. The control member 160 of the outer tubular member 110 is formed contiguous with the outer tubular member 110 and is not separate like control member 30 shown in FIGS. 1 and 2. The control member 160 can be considered part of the outer tubular member 110. Preferably, the control member 160 includes a groove 162 along its length. The groove 162 engages with one or more guide pins 24 in the handle member 4. In addition, the control member 160 preferably includes teeth 164 along a portion of its length. In this embodiment, the control member 160 passes directly into the control member guide 16. The teeth 164 of the control member 160 engage with teeth 57 of gear 56. In this aspect, the outer tubular member 110 directly engages with the gear 56 of the shaft 54. The shaft 54 is in rotational engagement with the outer tubular member 110.

It should be understood that various modifications of the above-described device are intended to fall within the scope of the claims. For example, it is possible to eliminate the wheel portion 52 of the control knob 50 and control rotational motion by direct manipulation of the shaft 54. Also, while a gear and tooth arrangement has generally been described as coupling movement of the shaft 54 with the control member guides 30, 160, alternative mechanisms can be employed. For example, various gear, screw, and even friction-based arrangements may be employed to translate unidirectional rotational motion of the shaft 54 into linear translation of the outer tubular member 110. While embodiments of the present invention have been shown and described, various modifications may be made without departing from the scope of the present invention. The invention, therefore, should not be limited, except to the following claims, and their equivalents.

What is claimed is:

1. A system for delivering an endoluminal prosthesis within a body lumen of a patient, comprising:
- a handle member;
- a control member slidably coupled to the handle member;
- an outer tubular member extending distally from the control member;
- an elongate inner member slidably disposed within the outer tubular member and axially fixed with respect to the handle member;
- a shaft rotatably mounted to the handle member, the shaft including a gear coupled to the control member such that rotation of the shaft displaces the outer tubular member axially with respect to the elongate inner member; and
- a uni-directional mechanism that limits rotation of the shaft to only one direction, such that when the shaft is rotated in the one direction, the outer tubular member is directed from a distal position to a proximal position.

2. The system of claim 1, further comprising a prosthesis within the outer tubular member proximate its distal end.

3. The system of claim 2, wherein the prosthesis is deployed from the distal end of the outer tubular member by rotation of the shaft in the one direction.

4. The system claim 1, wherein the control member further comprises a rail portion for engaging the gear of the shaft, and an engagement portion at a distal end of the rail portion for coupling the outer tubular member to the control member.

5. The system of claim 4, wherein the rail portion includes a plurality of teeth thereon, and the gear includes a plurality of teeth thereon for engaging with the teeth of the rail portion.

6. The system of claim 4, wherein the rail portion includes a groove disposed thereon, and the handle member includes at least one guide pin therein, the at least one guide pin engaging with the groove contained in the rail portion.

7. The system of claim 1, wherein the shaft is oriented substantially perpendicular to the control member.

8. The system of claim 1, wherein the handle member includes an inner member recess for securing the elongate inner member to the handle member.

* * * * *